(12) United States Patent
Bille

(10) Patent No.: US 7,662,149 B2
(45) Date of Patent: *Feb. 16, 2010

(54) CUSTOMIZED CORNEAL FLAP

(75) Inventor: Josef Bille, Heidelberg (DE)

(73) Assignee: Technolas Perfect Vision GmbH, Munich (DE)

(*) Notice: Subject to any disclaimer, the term of this patent is extended or adjusted under 35 U.S.C. 154(b) by 755 days.

This patent is subject to a terminal disclaimer.

(21) Appl. No.: 11/190,052

(22) Filed: Jul. 26, 2005

(65) Prior Publication Data

US 2006/0173445 A1    Aug. 3, 2006

Related U.S. Application Data

(63) Continuation-in-part of application No. 11/033,967, filed on Jan. 12, 2005, now Pat. No. 7,232,436, which is a continuation-in-part of application No. 10/293,226, filed on Nov. 13, 2002, now Pat. No. 6,887,232.

(51) Int. Cl.
A61B 18/20 (2006.01)

(52) U.S. Cl. .................. 606/5; 606/4; 128/898

(58) Field of Classification Search ........... 606/4–6, 606/10–12; 351/205–212; 128/898
See application file for complete search history.

(56) References Cited

U.S. PATENT DOCUMENTS

| 4,391,275 A | 7/1983 | Fankhauser et al. |
|---|---|---|
| 4,718,418 A | 1/1988 | L'Esperance, Jr. |
| 4,721,379 A | 1/1988 | L'Esperance |
| 4,770,172 A | 9/1988 | L'Esperance, Jr. |
| 4,907,586 A | 3/1990 | Bille et al. |
| 4,988,348 A | 1/1991 | Bille |
| 5,777,719 A * | 7/1998 | Williams et al. ............ 351/212 |
| 6,050,687 A | 4/2000 | Bille et al. |
| 6,095,651 A * | 8/2000 | Williams et al. ............ 351/246 |
| 6,302,877 B1 * | 10/2001 | Ruiz ............................. 606/5 |
| 6,428,533 B1 * | 8/2002 | Bille ............................ 606/11 |
| 6,641,577 B2 * | 11/2003 | Bille ............................. 606/4 |
| 6,805,694 B2 * | 10/2004 | Donitzky ....................... 606/5 |
| 6,887,232 B2 * | 5/2005 | Bille ............................. 606/5 |
| 7,232,436 B2 * | 6/2007 | Bille ............................. 606/5 |

* cited by examiner

*Primary Examiner*—Ahmed M Farah
(74) *Attorney, Agent, or Firm*—Nydegger & Associates

(57) ABSTRACT

A method and system for customizing a flap created from a transparent material compensates for aberrations, particularly higher order aberrations, which are pre-existing or otherwise induced during creation of the flap. Before flap creation, the distorted wavefront of the transparent material is determined and the topology of the transparent material is defined in order to predict contributions likely to be encountered or induced by the stress distribution during creation of the flap. In view of the topology of the transparent material, a prototypic dissection path based on the distorted wavefront is refined to establish a refined dissection path. As a result, the flap is created along the refined dissection path to correct and minimize or eliminate the formation of higher order aberrations.

9 Claims, 3 Drawing Sheets

CUSTOMIZED CORNEAL FLAP

This application is a continuation-in-part of pending application Ser. No. 11/033,967 filed Jan. 12, 2005, now U.S. Pat. No. 7,232,436 which is, in turn, a continuation-in-part of application Ser. No. 10/033,226 filed Nov. 13, 2002 now U.S. Pat. No. 6,887,232, which issued on May 3, 2005. The contents of application Ser. No. 11/033,967 and U.S. Pat. No. 6,887,232 are incorporated herein by reference.

FIELD OF THE INVENTION

The present invention pertains generally to methods and systems used in corrective optical surgery. More particularly, the present invention pertains to methods and systems that create a flap in the cornea during corrective optical surgery. The present invention is particularly, but not exclusively, useful as a method and system in which the anatomical conditions of a patient's eye are used to predict the effects of the creation of a corneal flap and to provide a surgical plan that compensates for such effects.

BACKGROUND OF THE INVENTION

In the perfect eye, an incoming beam of light is focused through the cornea and through the crystalline lens in a way that causes all of the light from a point source to converge at the same spot on the retina of the eye. This convergence occurs because all of the optical path lengths, for all light in the beam, are equal to each other. Stated differently, in the perfect eye, the time for all light to transit through the eye will be the same regardless of the particular path that is taken by the light.

Not all eyes, however, are perfect. The consequences of this are that light path lengths through the eye become distorted and are not all equal to each other. Thus, light from a point source that transits through an imperfect eye will not necessarily be focused on the retina, or to the same spot on the retina.

Normally, as light enters and passes through an eye it is refracted at the anterior surface of the cornea, at the posterior surface of the cornea, and at the surfaces of the crystalline lens. After all of these refractions have occurred, the light finally reaches the retina. As indicated above, in the case of the perfect eye, all of these refractions result in no overall change in the optical path lengths of light in the incoming beam. Therefore, any deviations resulting in unequal changes in these optical path lengths are indicative of imperfections in the eye that may need to be corrected.

In general, vision difficulties in the human eye can be characterized by the changes and differences in optical path lengths that occur as light transits through the eye. These difficulties are not uncommon. Indeed, nearly one half of the world's population suffers from imperfect visual perception. For example, many people are nearsighted because the distance between the lens and retina is too long (myopia). As a result, the sharp image of an object is generated not on the retina, but in front of or before the retina. Therefore, for a myopic person a distant scene appears to be more or less blurred. On the other hand, hyperopia is a condition wherein the error of refraction causes rays of light entering the eye parallel to the optic axis to be brought to a focus behind the retina. This happens because the distance between the lens and retina is too short. This condition is commonly referred to as farsightedness. Unlike the myopic person, a hyperopic, or farsighted, person will see a near scene as being more or less blurred.

Another refractive malady is astigmatism. Astigmatism, however, is different than either myopia or hyperopia in that it results from an unequal curvature of the refractive surfaces of the eye. With astigmatism, a ray of light is not sharply focused on the retina but is spread over a more or less diffuse area.

Further, in addition to the more simple refractive errors mentioned above, the human eye can also suffer from higher order refractive errors ("aberrations") such as coma, trefoil and spherical aberration. More specifically, coma is an aberration in a lens or lens system whereby an off-axis point object is imaged as a small pear-shaped blob. Coma can be described as a wavefront shape with twofold symmetry and is caused when the power of the zones of the lens varies with distance of the zone from the axis. Likewise, trefoil is described as a wavefront shape having threefold symmetry. Spherical aberration results from loss of definition of images that are formed by optical systems, such as an eye. Such aberrations arise from the geometry of a spherical surface. For these higher order aberrations ("HOAs"), an ideally flat 'wavefront' (i.e. a condition wherein all optical path lengths are equal) is distorted by a real-world optical system. In some cases, these distortions occur in a very complex way. In the trivial case, non-higher order distortions like nearsightedness and farsightedness would result in an uncomplicated bowl-like symmetrical distortion. With HOAs, however, the result is a complex non-symmetrical distortion of the originally flat wavefront. It is these non-symmetrical distortions which are unique for every optical system (e.g., a person's eye), and which lead to blurred optical imaging of viewed scenes.

While a typical approach for improving the vision of a patient has been to perform refractive surgery on the eye to eliminate distortions, the surgery itself can lead to an increase in HOAs, both immediately and during recovery. Indeed, it has been determined that conditions such as biomechanical stress distribution and hydration levels can induce changes in the optical characteristics of an eye as a mere consequence of corneal dissection. Specifically, the creation of a flap in the cornea by a mechanical microkeratome can induce HOAs including vertical coma, horizontal coma, spherical aberration and 90/180° astigmatism. While inducing fewer HOAs, the use of femtosecond lasers to create a flap in the cornea has not led to the complete elimination of such changes.

In general, when a corneal flap is created for purposes of performing refractive surgery, HOAs can result from two distinctly different circumstances. For one, HOAs can be physically introduced during the actual creation of the flap. As mentioned above, these HOAs typically result from the redistribution of biomechanical stresses that occur in the cornea as the flap is being created. For another, HOAs also result from physical characteristics of the cornea, and from the eye itself. For example, it is known that decentration (i.e. a condition wherein the anatomical and optical axes of the eye are not properly aligned) will create HOAs. Regardless of their source, however, HOAs can be troublesome and, if possible, should be corrected.

In light of the above, it is an object of the present invention to provide a method and system that measures the topology of the cornea, or other transparent material, in order to predict the effect of the creation of a flap thereon on HOAs. Another object of the present invention is to provide a method and system that incorporates the anatomical conditions in the cornea into surgical planning to compensate for surgically induced changes in HOAs. Another object of the present invention is to provide a method and system that incorporates pre-flap-creation wavefront data into the dimensional planning of the flap. Yet another object of the present invention is to provide a method and system that uses a real-time, closed-loop, adaptive-optical control system to reposition the transparent material during flap creation to match the pre-flap-creation optical conditions. Still another object of the present invention is to provide a method and system for predicting and precompensating for changes in HOAs induced by flap creation which are effectively easy to use, relatively simple to operate and implement, and comparatively cost effective.

SUMMARY OF THE INVENTION

In the present invention, a system is provided for creating a customized flap in a transparent material, such as in the cornea of an eye, via photoablation. More specifically, the system of the present invention creates such a flap while compensating for higher order aberrations otherwise induced during flap creation.

Structurally, the system of the present invention includes two distinct laser sources. One is for generating a diagnostic laser beam. The other is for generating an ablation laser beam that will be used to photoablate corneal tissue during creation of the flap. Along with the two laser sources, the system typically includes an active mirror and a detector. More specifically, the active mirror comprises a plurality of separate reflective elements for individually reflecting respective component beams of the diagnostic beam. Together, these elements of the active mirror are used, in concert, to direct the diagnostic laser beam to a focal spot on the retina of the eye. The detector is then used to receive the diagnostic beam after it has been reflected from the retina. The system further includes a comparator and compensator that are used with the detector during operation of the ablation laser beam, as discussed below.

In the operation of the present invention, diagnostic measurements are initially made. Specifically, the distorted wavefront of the patient's eye is determined. To do this, the diagnostic laser beam is passed through the patient's eye, reflected by the patient's retina and received by the detector. The reflected laser beam is properly considered to include a plurality of individual component beams. Collectively, these constituent component light beams define a wavefront for the larger inclusive light beam. For the present invention, the wavefront that is received by the detector, and that results from passing through the stroma of an uncorrected eye is considered to be a "distorted wavefront." Thus, a distorted wavefront exhibits the actual real-time characteristics of the cornea.

After the distorted wavefront has been determined, wavefront analysis is also performed to define the topology of the patient's cornea. As used herein, "topology" means all physical characteristics of the cornea, or other transparent material, and preferably includes stromal bed thickness, total corneal pachymetry, optical density, characteristics affecting biomechanical stresses in the cornea, and dimensions of the planned dissection.

Based on the distorted wavefront, a prototypic dissection path for creation of the corneal flap is identified. Specifically, the prototypic dissection path is identified by comparing the distorted wavefront with a "desired wavefront." For the purposes of the present invention, the distorted wavefront is obtained as disclosed above, and the desired wavefront is planar or substantially planar. In any event, the desired wavefront is the objective of the required refractive surgical procedure. As envisioned for the present invention, during the identification of the prototypic dissection path, no consideration is given to the topology of the cornea.

Once the topology of the cornea has been defined and the prototypic dissection path has been identified, the two are then used together to predict whether HOAs will be induced or affected by cutting corneal tissue along the prototypic dissection path. Beyond this, the topology of the cornea can also be used to identify any pre-existing HOAs that may be present. After these predictions and identifications have been made, the prototypic dissection path can be refined to compensate for the predicted effects of the topology. For the present invention, this refinement is essentially a two-step process. In the first step, the prototypic dissection path is refined in order to eliminate or minimize the inducement of HOAs that may result during the laser surgical procedure. In the second step, the refined prototypic dissection path may then be even further refined to correct for pre-existing HOAs. In this manner, the present invention compensates for both topological and anatomical effects on HOAs.

In accordance with the present invention, the initial prototypic dissection path is essentially established as a path between two selected points in the cornea. This path may or may not be linear, and it is established as a succession of substantially contiguous locations where laser induced optical breakdown (LIOB) is accomplished. As indicated above, this initial prototypic dissection path is identified for the purpose of performing the required refractive surgery. As also indicated above, in order to account for HOAs, the prototypic dissection path needs to be refined. Depending on topological and anatomical considerations, refinement of the prototypic dissection path may require a two-step process as suggested above.

For the present invention, HOAs that may be induced when corneal tissue is cut during a laser surgical procedure are minimized or eliminated by appropriately altering the course of the prototypic dissection path. In particular, by altering the course of the prototypic dissection path, the refined prototypic dissection path can be established to accommodate the redistribution of biomechanical stresses in the cornea that would otherwise result when the corneal tissue is cut. Without more, however, course alteration alone will not correct for the pre-existing HOAs.

If an evaluation of the cornea and the eye reveals pre-existing HOAs, the refined prototypic dissection path discussed above needs to be further refined. Specifically, using the initially refined prototypic dissection path as a base line, further refinement of the refined prototypic dissection path requires performing additional LIOB. In particular, the necessary additional LIOB is performed at lateral locations that are directed perpendicularly from selected points on the prototypic dissection path. As envisioned for the present invention, this additional LIOB is intended to remove tissue that will correct the non-induced (pre-existing) HOAs. Stated differently, if used, the second step in creating the refined prototypic dissection path results in altering the actual width of the prototypic dissection path to account for the non-induced (pre-existing) HOAs.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION OF THE PREFERRED EMBODIMENTS

Figure 1:
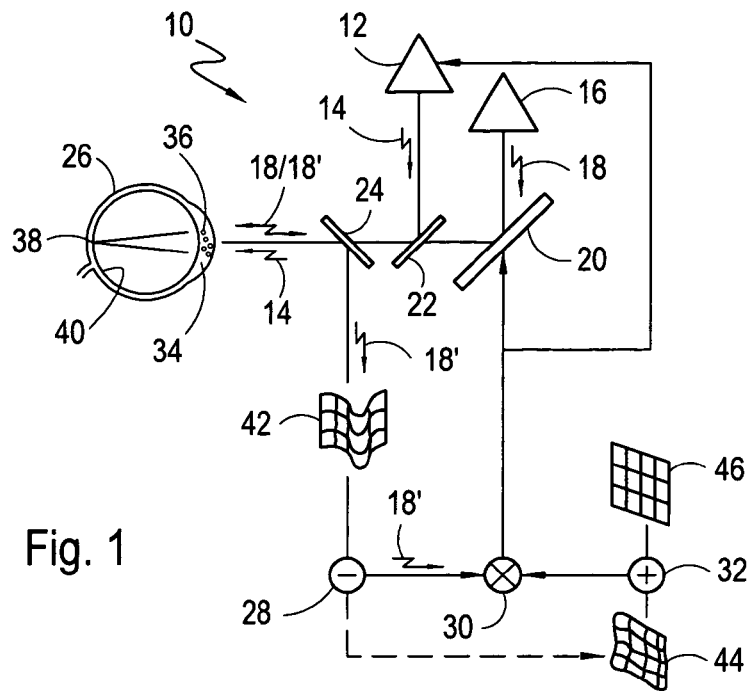
FIG. 1 is a schematic layout showing the interrelationships of components in a system for creating a customized corneal flap in accordance with the present invention.

Referring initially to FIG. 1, a system for creating a customized corneal flap in accordance with the present invention is shown and is generally designated 10. In detail, the components of system 10 include a source 12, such as a femtosecond laser, for generating an ablation laser beam 14, and a source 16 for generating a diagnostic laser beam 18. Further, the system 10 includes an active, multi-facet mirror 20, a beam splitter 22 and a beam splitter 24. More particularly, the active mirror 20 is preferably of a type disclosed in U.S. Pat. No. 6,220,707 which issued to Bille for an invention entitled "Method for Programming an Active Mirror to Mimic a Wavefront" and which is assigned to the same assignee as the present invention. As shown, the active mirror 20 and the beam splitters 22 and 24 direct the diagnostic laser beam 18 from the diagnostic laser source 16 toward an eye 26. Likewise, the beam splitters 22 and 24 are used to direct the ablation laser beam 14 from the ablation laser source 12 toward the eye 26.

FIG. 1 also shows that the system 10 of the present invention includes a detector 28, a comparator 30 and a compensator 32. In particular, the detector 28 is preferably of a type commonly known as a Hartmann-Shack sensor. The comparator 30 and compensator 32 are electronic components known in the pertinent art that will perform the requisite functions for the system 10.

Figure 6:
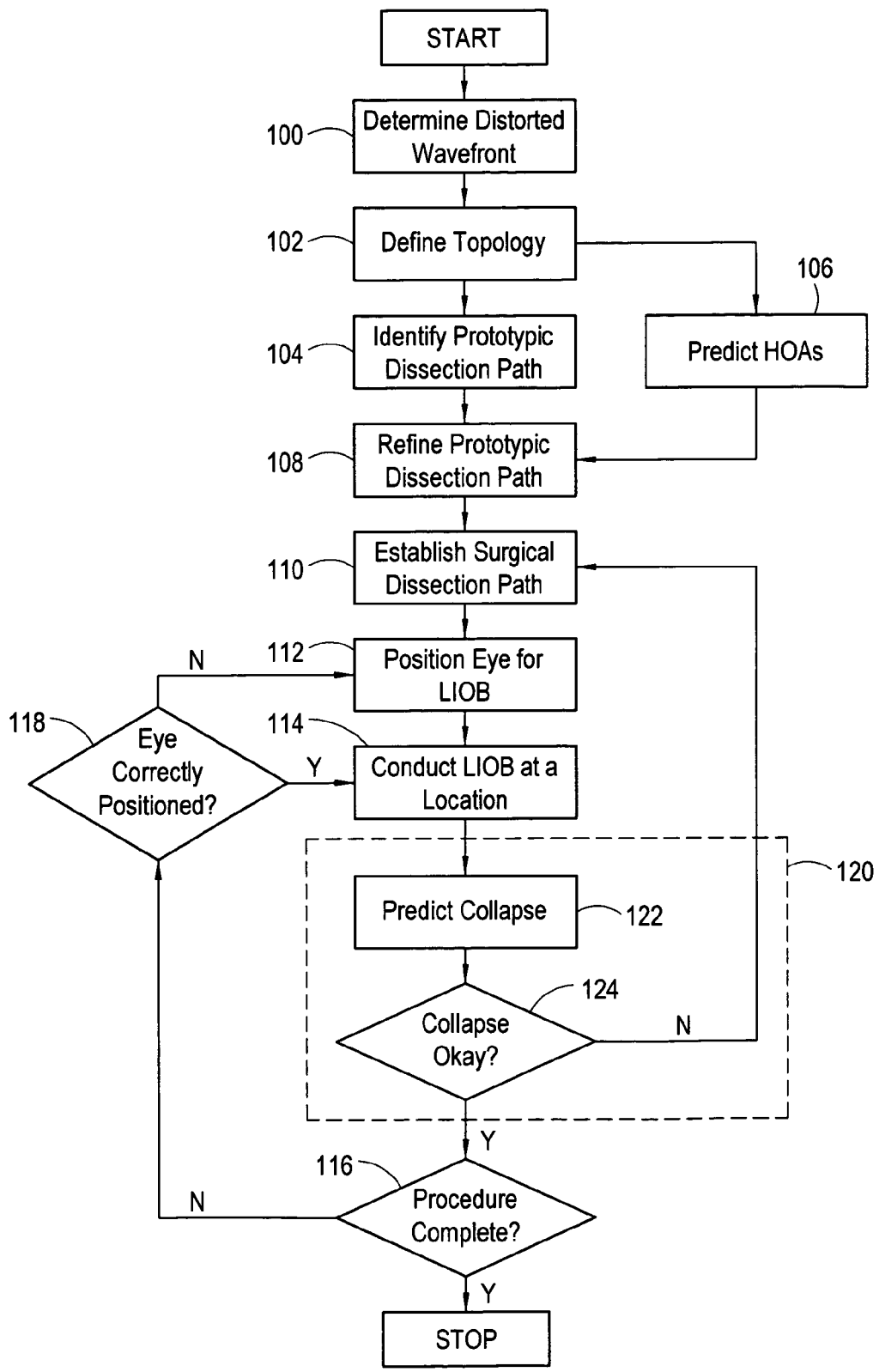
FIG. 6 is a functional flow chart illustrating the method for creating a customized corneal flap in accordance with the present invention.

Cross-referencing FIG. 1 with FIG. 6, it is to be appreciated and understood that the system 10 is used to make initial diagnostic evaluations of a patient's cornea 34, and in particular its stromal tissue 36. Specifically, the diagnostic laser beam 18 is focused (by optical components not shown) to a focal spot 38 on the retina 40 of the patient's eye 26. As shown in FIG. 1, the reflected diagnostic laser beam 18' passes through the cornea 34, exits the eye 26, and is directed by the beam splitter 24 toward the detector 28. Using wavefront analysis, the system 10 analyzes the reflected diagnostic laser beam 18' received by the detector 28 to determine the distorted wavefront 42 of the uncorrected eye 26 as shown in action block 100 of FIG. 6. When using wavefront analysis considerations, the reflected diagnostic beam 18' is conceptually considered as including a plurality of individual and separate laser beam components. Together, these components are characterized as a distorted wavefront 42 that results from the uncorrected eye 26 as a consequence of light passing through the stromal tissue 36. FIG. 1 further shows a desired wavefront 46. This desired wavefront 46 is typically either a plane wavefront, or a wavefront that is substantially similar to a plane wavefront. In any event, it is the desired wavefront 46 that is the objective of a vision correction surgery that uses the procedure performed by the system 10.

For the present invention, wavefront analysis of the reflected diagnostic beam 18' is further utilized to define the topology of the cornea 34. This step is shown at action block 102 of FIG. 6. As stated above, the "topology" of the cornea 34 refers to the cornea's physical properties, including stromal bed thickness, total corneal pachymetry, optical density, the biomechanical stress distribution in the cornea, as well as the dimensions of the planned dissection. Such properties are ascertained from the reflected diagnostic beam 18'. While wavefront technology is used to define the topology of the cornea 34 in the presently described embodiment, other techniques such as ellipsometry, second harmonic generation (SHG) microscopy, confocal microscopy, corneal topography, optical coherence tomography (OCT), or ultrasonic pachymetry may be used. In any case, after the topology of the cornea 34 is defined it is used during surgical planning as discussed below.

Figure 3:
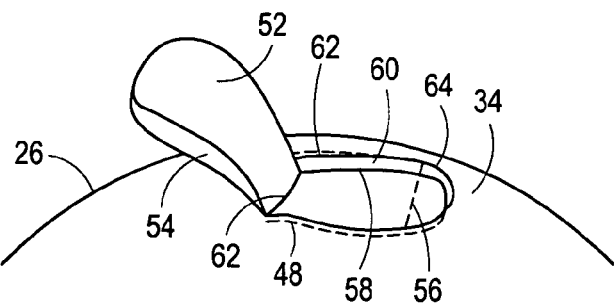
FIG. 3 is a perspective view of a corneal flap.
Figure 4:
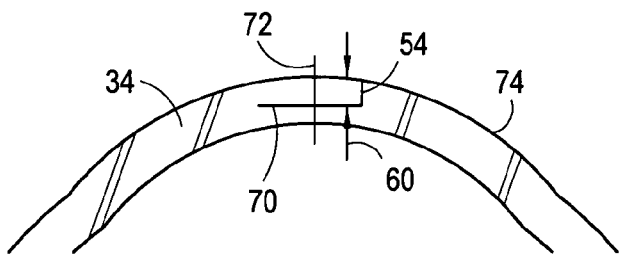
FIG. 4 is a sectional view of a cornea after the periphery and edge of a flap have been established.
Figure 5:
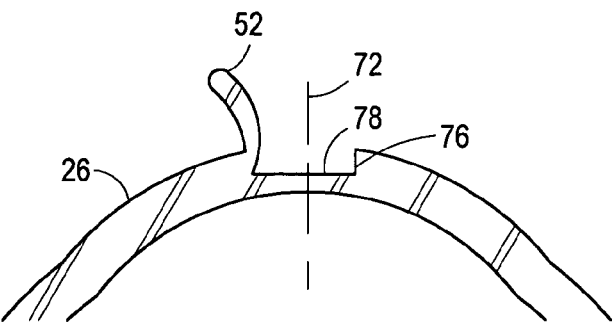
FIG. 5 is a sectional view of a corneal flap, after the flap has been peeled back from the remainder of the cornea.

As shown in FIG. 6, a prototypic dissection path for the customized corneal flap is identified in action block 104. Such identification is based on a comparison between the distorted wavefront 42 and the desired wavefront 46 as depicted in FIG. 1 and is designed to compensate for pre-existing lower order aberrations such as myopia, hyperopia, or astigmatisms. During identification of the prototypic dissection path 48 (shown in FIG. 3), dimensions are preferably established for the flap 52 (also shown in FIG. 3). Referring to FIGS. 3-5, these flap dimensions include an edge slope 54, a flap-diameter 56, a flap-shape 58, a flap-thickness profile 60, and a hinge-position 62.

Referring now to the topology defined in action block 102, FIG. 6 shows at action block 106 that the topology of the cornea 34 is used to predict whether HOAs will be induced or affected by the creation of a corneal flap 52 along the prototypic dissection path 48. For instance, the system 10 may consider the prototypical dissection path 48 and the pre-surgery physical properties of a patient's cornea 34 and predict a specific increase in trefoil HOAs due to the effects of the prescribed incision on the cornea 34.

In order to minimize the occurrence of HOAs resulting from the creation of the flap 52, the system 10 uses the predicted HOAs to refine the prototypic dissection path 48 (as shown at action block 108). As a result of this step, the system 10 establishes a surgical or refined dissection path 64 (shown in FIG. 3) that compensates for contributions otherwise induced by the biomechanical stress distribution of the cornea 34 during creation of the flap 52. By compensating for the topological contributions, the refined dissection path 64 eliminates or minimizes the formation of HOAs resulting from creation of the flap 52. Further, compensation for the topological contributions may be provided by the localized ablation of extra amounts of stromal tissue along the refined dissection path 64 via multiple laser passes. Such ablation may result in changes in the biomechanical force distribution and corresponding distortions of the stromal surface topology. The step of establishing the surgical or refined dissection path 64 is shown at action block 110 in FIG. 6.

Figure 2:
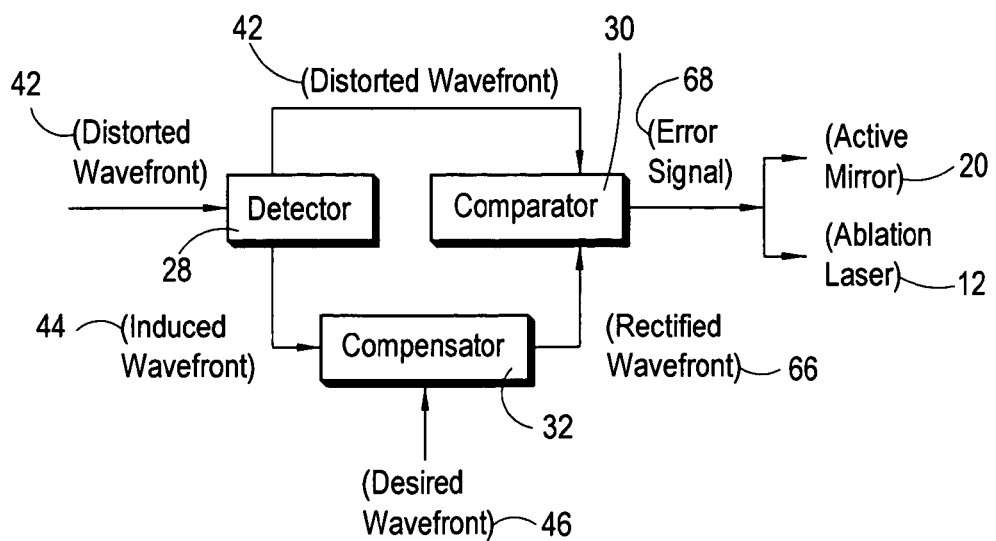
FIG. 2 is a functional representation of the wavefront analysis techniques used in the operation of the system of the present invention.

After the refined dissection path 64 is established, refractive surgery may be performed. To prepare for surgery, the patient is positioned such that the system 10 and the eye 26 are generally in the same relative position as when the initial diagnosis was made (action block 112). In order to ensure proper positioning, a real-time closed-loop adaptive-optical control system as shown in FIG. 2 is used. Specifically, as discussed above, a diagnostic laser beam 18 is focused on the patient's retina 40. The diagnostic laser beam 18' reflected therefrom is directed to the detector 28 as a distorted wavefront 42. This distorted wavefront 42 is compared to the initially diagnosed distorted wavefront (not shown, but known by comparator 30) to generate an error signal 68. In response to the error signal 68, the relative position of the patient's eye 26 and the system 10 is modified. Then, the system 10 passes another diagnostic laser beam 18 through the eye 26 to determine a "new" distorted wavefront 42. This process is continued until it is concluded that the eye 26 is in the same relative position with respect to the system 10 as during the diagnosis.

Referring to FIG. 6, it is seen that, after the eye 26 is properly positioned, laser induced optical breakdown (LIOB), or photoablation, is conducted at a location along the refined dissection path 64 (action block 114). Specifically, the ablation laser beam 14 is directed to a focal point along the refined dissection path 64 to cause photoablation. While photoablation is preferably used, the present invention contemplates that any type of dissection may be performed.

As shown in inquiry block 116, if the procedure is complete after photoablation of the corneal tissue at the targeted location, i.e., if creation of the flap 52 is complete, then the surgery is stopped. If, however, the procedure is not complete, then further photoablation is required. As shown in inquiry block 118, before further photoablation occurs, it is determined whether the eye 26 is still properly positioned. If it is not, the eye 26 is repositioned at action block 112. If the eye 26 is correctly positioned, the system 10 directs the ablation laser beam 14 to a different location along the refined dissection path 64 and conducts LIOB at the new location. In order to ensure proper photoablation along the refined dissection path 64, the system 10 controls the location of the focal point of the ablation laser beam 14 in response to the detector's receipt of the distorted wavefronts 42 from the reflected diagnostic laser beam 18'. In other words, the continuously updated distorted wavefronts 42 show what locations in the cornea 34 have been fully photoablated. As a result, the system 10 moves the focal point of the ablation laser beam 14 to locations along the refined dissection path 64 that still require photoablation. This process is repeated until creation of the customized flap 52 is completed. While the system 10 is illustrated as using wavefront technology, it is contemplated herein that other measurement techniques such as ellipsometry, second harmonic generation microscopy, confocal microscopy, or other techniques can be used to provide monitoring of the creation of the flap.

As is further shown in FIG. 6, the present invention may include an optional operational loop 120. This operational loop 120 is of particular importance when bubbles formed in the stromal tissue 36 may affect HOAs. It is to be appreciated and understood that during an intrastromal photoablation procedure, gas bubbles form as a consequence of photoablation of the stromal tissue 36. When bubbles formed in the stromal tissue 36 do not collapse, they cause aberrations that affect the distorted wavefront 42 received by the detector 28. Based on the topology of the cornea 34, the collapse of bubbles formed in the stromal tissue 36 may be predicted as shown at action block 122. However, if a bubble behaves differently than as predicted, HOAs may be affected. As a result, inquiry block 124 requires that in cases where bubbles do not behave as predicted, the refined dissection path is re-established at action block 110 in order to take into consideration such behavior. If the bubbles behave as predicted, the operation moves from inquiry block 124 to inquiry block 116.

Referring now to FIG. 2, it will be appreciated that in the operation of the system 10 the detector 28 first receives the distorted wavefront 42. Using the refined dissection path 64 and the predicted bubble behavior, the detector 28 generates an induced wavefront 44. As used herein, an "induced wavefront" results from the formation of bubbles in the stroma, and includes the distorted wavefront 42. The compensator 32 then alters the predetermined, desired wavefront 46 with this induced wavefront 44. This alteration creates a rectified wavefront 66. As used herein, the "rectified wavefront" results from incorporating an induced wavefront with a desired wavefront. The rectified wavefront 66 is then compared with the distorted wavefront 42 to generate an error signal 68. In turn, this error signal 68 is used to manipulate the active mirror 20 for control of the diagnostic laser beam 18. Importantly, the error signal 68 is also used to activate the ablation laser source 12 and, specifically, the error signal 68 causes the ablation laser source 12 to cease its operation when the error signal 68 is a null.

Referring now to FIGS. 3-5, a corneal flap 52 prepared in accordance with the present invention is shown. As shown in FIG. 4, the flap 52 is prepared by first cutting a periphery 70 for the flap 52 in accordance with the refined dissection path 64. A typical periphery 70 follows a curved line that is centered approximately on the optical axis 72 of the eye 26 and extends through an arc of about two hundred and seventy degrees. With the periphery 70 established, an incision extending from the anterior surface 74 of the cornea 34 to the periphery 70 can be made along the refined dissection path 64 to establish an edge 76 for the flap 52. Once the edge 76 is created, the flap 52 can be peeled from the remainder of the cornea 34 to expose a bed of stromal tissue 78. After exposure, the bed of stromal tissue 78 can be photoablated using an excimer laser (not shown). After photoablation with the excimer laser, the flap 52 can be repositioned over the bed of stromal tissue 78 and allowed to heal. The result is a reshaped cornea 34.

Figure 7A:
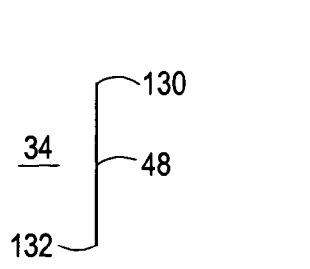
FIG. 7A is an exemplary prototypic dissection path.
Figure 7B:
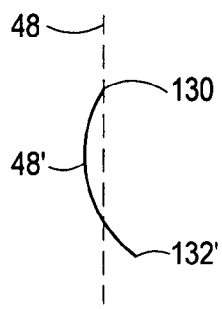
FIG. 7B is a refined dissection path, including alterations to the course of the prototypic dissection path shown in FIG. 7A that are introduced to compensate for higher order aberrations otherwise induced during a surgical procedure.
Figure 7C:
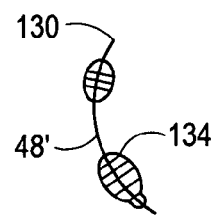
FIG. 7C is a refined dissection path as shown in FIG. 7B with further refinements introduced to compensate for pre-existing higher order aberrations.

In light of the above, the actual methodology used by system 10 to compensate for higher order aberrations (HOAs) will be best appreciated by reference to FIGS. 7A-C. Beginning with FIG. 7A, it is to be appreciated that any prototypic dissection path 48 in a cornea 34 will essentially be a locus of points that extend between a start point 130 and an end point 132. The fact that the particular prototypic dissection path 48 shown in FIG. 7A happens to be a straight line, is only exemplary. As will be appreciated by the skilled artisan, the prototypic dissection path 48 may be linear or non-linear and, in actuality, a plurality of dissection paths 48 may need to be followed to perform the objective of a desired surgical procedure. In any event, and as discussed above in detail, the prototypic dissection path 48 is initially determined with a view toward performing the necessary refractive surgery. This, however, can be done without specific regard to the presence or inducement of higher order aberrations (HOAs). Nevertheless, because HOAs may pre-exist in the cornea 34, or may be induced during the refractive surgery, the prototypic dissection path 48 may need to be somehow altered to account for them.

Based on the topology of the cornea 34, and in view of the prototypic dissection path 48 that is required for refractive surgery, the present invention envisions refining the dissection path 48 to account for HOAs that may be induced during the surgical procedure. In particular, as illustrated in FIG. 7B, the minimization or elimination of induced HOAs can be accomplished by appropriately altering the course of the prototypic dissection path 48. For example, as shown in FIG. 7B, this might be done by creating a refined prototypic dissection path 48' that is appropriately curved, and that extends from the start point 130 to a new end point 132'. The deviations, in this exemplary case, are seen in FIG. 7B by comparing the initial prototypic dissection path 48 (shown as a dashed line) with the refined prototypic dissection path 48'. As indicated above, the refined prototypic dissection path 48' is used to minimize or eliminate HOAs that may be induced by the surgical procedure.

It can sometimes happen that, before surgery, the cornea 34 has pre-existing HOAs. For instance, such HOAs as might be anatomically caused by a decentration (i.e. the optical and anatomical axes of the eye 26 are not properly aligned), or they can result from the topology of the eye 26. If so, the process for refining the prototypic dissection path 48 becomes, essentially, a two-step procedure. Specifically, once the refined prototypic dissection path 48' is determined (the first step), additional laser induced optical breakdown (LIOB) may be required (the second step). In detail, as best seen in FIG. 7C, this second step can be accomplished by photoablating tissue along a plurality of lines 134 that are oriented perpendicular to the refined prototypic dissection path 48'. As a practical matter, the cumulative effect of this results in widening the refined prototypic dissection path 48' at selected locations along the length of the path 48'. As indicated above, the additional LIOB that is included with the refined prototypic dissection path 48' is used to correct pre-existing HOAs that may be present before the surgical procedure is performed.

While the particular method and system for creating a Customized Corneal Flap as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims. It will be appreciated that the methods and systems of the present invention can be applied to any transparent material.

What is claimed is:

1. A method for customizing a flap created from a substantially transparent material, the method comprising the steps of:

defining a topology for the material wherein the topology includes a stress distribution;

identifying a prototypic dissection path through the material for creation of the flap;

refining the prototypic dissection path to compensate for the topology to establish a refined dissection path, wherein the refined dissection path compensates for contributions otherwise induced by the stress distribution from the topology of the transparent material during creation of the flap; and dissecting the material along the refined dissection path with a laser to create a flap in the material.

2. A method as recited in claim 1 further comprising the step of determining a refractive state of the material.

3. A method as recited in claim 2 wherein the refined dissection path compensates for said refractive features and for the contributions otherwise induced by the topology of the transparent material during creation of the flap.

4. A method as recited in claim 1 wherein the dissecting step is accomplished using a femtosecond laser system.

5. A method as recited in claim 1 wherein the defining step is accomplished by using wavefront data.

6. A method as recited in claim 5 wherein wavefront data is used to establish dimensions for the flap in the identifying step.

7. A method as recited in claim 6 wherein the flap dimensions include a flap-thickness-profile, a hinge-position, an edge slope, a flap-diameter and a flap-shape.

8. A method as recited in claim 6 wherein the wavefront data is used in the refining step.

9. A method as recited in claim 8 further comprising the step of repositioning the transparent material during the dissecting step to maintain dissection along the refined dissection path, the repositioning step being performed by a real-time, closed loop, adaptive-optical control system.

\* \* \* \* \*